United States Patent [19]
Grabstein et al.

[11] Patent Number: 5,747,024
[45] Date of Patent: May 5, 1998

[54] VACCINE ADJUVANT COMPRISING INTERLEUKIN-15

[75] Inventors: Kenneth H. Grabstein, Mercer Island; Michael B. Widmer, Seattle, both of Wash.

[73] Assignee: Immunex Corporation, Seattle, Wash.

[21] Appl. No.: 504,042

[22] Filed: Jul. 19, 1995

Related U.S. Application Data

[63] Continuation-in-part of Ser. No. 393,305, Feb. 22, 1995, Pat. No. 5,574,138, which is a continuation-in-part of Ser. No. 233,606, Apr. 22, 1994, abandoned, which is a continuation-in-part of Ser. No. 31,399, Mar. 8, 1993, Pat. No. 5,552,303.

[51] Int. Cl.⁶ ..................................................... A61K 38/20
[52] U.S. Cl. ............................. 424/85.2; 514/2; 514/8; 514/12; 514/885; 424/278.1; 530/351
[58] Field of Search ............................. 424/85.2, 278.1; 514/2, 8, 12, 885; 530/351

[56] References Cited

PUBLICATIONS

Cohen Jon (1995) Science vol. 270 p. 908.

*Primary Examiner*—John Ulm
*Assistant Examiner*—Prema Mertz
*Attorney, Agent, or Firm*—Stephen L. Malaska; Christopher L. Wight

[57] ABSTRACT

Methods of enhancing a mammal's immune response to a vaccine antigen are disclosed. Interleukin-15 can be used as a vaccine adjuvant to enhance or potentiate the immune response to a vaccine. Compositions comprising an immunogenic amount of vaccine antigen and an immunogenicity-augmenting amount of IL-15 are also provided by the invention. IL-15 can be used alone in the invention or in concurrent or sequential combination with additional vaccine adjuvants.

10 Claims, No Drawings

VACCINE ADJUVANT COMPRISING INTERLEUKIN-15

CROSS-REFERENCES TO RELATED APPLICATIONS

This is a continuation-in-part of U.S. patent application Ser. No. 08/393,305, filed 22 Feb. 1995, now U.S. Pat. No. 5,574,138, which is a continuation-in-part of U.S. patent application Ser. No. 08/233,606, filed 22 Apr. 1994, now abandoned, which is a continuation-in-part of U.S. patent application Ser. No. 08/031,399, filed 8 Mar. 1993, now U.S. Pat. No. 5,552,303.

FIELD OF THE INVENTION

The invention pertains to the field of vaccines and in particular, to a composition that can augment the immunogenicity of a vaccine antigen.

BACKGROUND OF THE INVENTION

The objective of vaccination is to provide effective immunity by establishing adequate levels of antibody and a primed population of cells that can rapidly expand on renewed contact with antigen. The first contact with antigen during vaccination must not be injurious to the recipient and thus usually consists of pathogenically-deficient antigen.

A frequent difficulty with active immunization protocols is that the vaccine antigen does not possess sufficient immunogenicity to promote a strong immune response, and therefore a sufficient level of protection against subsequent challenge by the same antigen. In addition, certain antigens may elicit only weak cell-mediated or antibody response. For many antigens, both a strong humoral response and a strong cell-mediated response is desirable.

For decades, researchers have experimented with diverse compounds to increase the immunogenicity of vaccines. Immunopotentiators, also known as adjuvants, of vaccines are compositions of matter that facilitate a strong immune response to a vaccine. In addition, the relatively weak immunogenicity of certain novel recombinant antigens has required adjuvants to be more potent. Vaccine adjuvants have different modes of action, affecting the immune response both quantitatively and qualitatively. Such modes of action can be by mobilizing T cells, acting as depots and altering lymphocyte circulation so that these cells remain localized in draining lymph nodes. They may also serve to focus antigen at the site of immunization, thereby allowing antigen specific T cells and B cells to interact more efficiently with antigen-presenting cells. They may also stimulate proliferation and differentiation of T cells and have effects on B cells, such as enhancing the production of different Ig isotypes. Further, adjuvants may stimulate and affect the behavior of antigen-presenting cells, particularly macrophages, rendering them more effective for presenting antigen to T cells and B cells.

SUMMARY OF THE INVENTION

The invention is directed to a composition that is capable of augmenting the immunogenicity of a vaccine. The composition, or adjuvant, is administered to a mammal in need thereof in sequential or concurrent combination with the vaccine antigen. In particular, the adjuvant is a cytokine known as interleukin-15 ("IL-15"). IL-15 is a recently discovered cytokine, and is a potent T cell growth factor. IL-15 can cause the proliferation and differentiation of T cells in vitro and can augment T cell mediated immune response in vivo. In addition, IL-15 has been shown to stimulate the induction of B cell proliferation and differentiation. The proliferation and differentiation of antigen specific T cells and B cells can augment the protective immunity for a particular antigen. These properties of IL-15 make it a suitable adjuvant for a variety of vaccines wherein augmentation of the immune response to the antigen is desired. Administration of IL-15 in concurrent or sequential combination with a vaccine will prompt an enhanced immune response against the vaccine. Further included in the invention are compositions that comprise such an immunogenicity-augmenting amount of IL15 in combination with at least one other vaccine adjuvant, such as, for example, IL-2, IL-10, GM-CSF, G-CSF and CD40 ligand. Methods of vaccination that provide for the administration of an immunogenicity-augmenting amount of IL-15 and an immunogenicity-augmenting amount of another vaccine adjuvant are also provided by the invention.

DETAILED DESCRIPTION OF THE INVENTION

The invention is directed to a vaccine adjuvant, and its use in potentiating the immunogenicity of vaccines when administered to mammals. In particular, the invention is directed to the use of IL-15 to augment or potentiate the immune response to a vaccine antigen. Such augmentation or potentiation is useful to enhance the effectiveness of a vaccine, and thus can reduce the number of immunizations with antigen, and provide longer, more effective, immunity.

In general, the method of the invention comprises administering to a mammal an amount of IL-15 effective to augment or potentiate the immunogenicity of a vaccine. The L-15 adjuvant can be administered in concurrent or sequential combination with the vaccine.

IL-15 is a known T-cell growth factor that can support proliferation of an IL-2-dependent cell line, CTLL-2. IL-15 was first reported by Grabstein et al., in Science, 264:965 (1994), which is incorporated herein by reference, as a 114-amino acid mature protein. The cDNA of human IL-15 is shown in SEQ ID NO:1, whereas the amino acid sequence of human IL-15 is shown in SEQ ID NO:2. Armitage et al., J. Immunology, 154:483–490 (1995), reported that IL-15 potently induces IgM, IgG, and IgA secretion from activated human B cells.

The term, "IL-15" as used herein, means a polypeptide having at least 90% homology to the native amino acid sequence of SEQ ID NO:2; and muteins, analogs or subunits of the native polypeptides that are encoded by nucleic acids that bind to the nucleic acid sequence of SEQ ID NO:1 under conditions of moderate or high stringency, and each of which will stimulate proliferation of CTLL-2 cells (Gillis and Smith, Nature 268:154 (1977); ATCC TIB 214). In the CTLL-2 proliferation assays, supernatants of cells transfected with recombinantly expressed precursor and inframe fusions of mature forms of IL-15 can induce CTLL-2 cell proliferation. The term, IL-15, as used herein, also means IL-15 as derived from a variety of mammalian species, including, for example, human, simian, bovine, porcine, equine and murine. An IL-15 "mutein" or "variant", as referred to herein, is a polypeptide substantially homologous to a sequence of a native mammalian IL-15 but that has an amino acid sequence different from a native mammalian IL-15 polypeptide because of an amino acid deletion, insertion or substitution. Variants may comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Naturally occurring IL-15 variants are also encompassed by the invention. Examples of such variants are proteins that result from alternate mRNA splicing events or from proteolytic cleavage of the IL-15 protein, wherein the IL-15 binding property is retained. Alternate splicing of mRNA may yield a truncated but biologically active IL-15 protein. Variations attributable to proteolysis include, for example, differences in the N- or C-tertmini upon expression in different types of host cells, due to proteolytic removal of one or more terminal amino acids from the IL-15 protein (generally from 1-5 terminal amino acids).

Human IL-15 can be obtained according to the procedures described by Grabstein et al., *Science*, 264:965 (1994), or by conventional procedures such as polymerase chain reaction (PCR) based on DNA sequence information provided in SEQ ID NO:1. A deposit of human IL-15 cDNA was made with the American Type Culture Collection, Rockville, Md., USA (ATCC) on Feb. 19, 1993 and assigned accession number 69245. The deposit was named "I41-hIL-15." The deposit was made according to the terms of the Budapest Treaty.

As used herein, "vaccine" means an organism or material that contains an antigen in an innocuous form. The vaccine may be recombinant or non-recombinant. When inoculated into a non-immune host, the vaccine will provoke active immunity to the organism or material, but will not cause disease. Vaccines may take the form, for example, of a toxoid, which is defined as a toxin that has been detoxified but that still retains its major immunogenic determinants; or a killed organism, such as typhoid, cholera and poliomyelitis; or attenuated organisms, that are the live, but non-virulent, forms of pathogens, or it may be antigen encoded by such organism, or it may be a live tumor cell or an antigen present on a tumor cell.

The term "adjuvant" refers to a substance that enhances, augments or potentiates the host's immune response to a vaccine antigen.

The term "immunogenicity" means relative effectiveness of an immunogen or antigen to induce an immune response.

The IL-15 compositions of the invention can be formulated according to known methods used to prepare pharmaceutical compositions. IL-15 can be combined in admixture, either as the sole vaccine adjuvant material or with other known vaccine adjuvant materials, with pharmaceutically suitable diluents (e.g., Tris-HCl, acetate, phosphate), preservatives (e.g., Thimerosal, benzyl alcohol, parabens), emulsifiers, solubilizers, adjuvants and/or carriers. Suitable carriers or vehicles and their formulations are described in Remington's Pharmaceutical Sciences, 16th ed. 1980, Mack Publishing Co. In addition, IL-15 also can be specially formulated to provide a desired release profile into the host. Slow release formulations and controlled or sustained release formulations are varied and are well known in the art and give a wide variety of release profiles. IL-15 can be used in a slow release, controlled release or sustained release formulation for the purposes of the invention.

IL-15 also can be administered in combination with at least one other vaccine adjuvant. Many vaccine adjuvants exist and would likely be suitable for use in combination with IL-15, for example, cytokines are particularly preferred vaccine adjuvants. More preferred adjuvants include granulocyte-macrophage colony stimulating factor (GM-CSF), granulocyte colony stimulating factor (G-CSF), IL-2, IL-4, IL-10 and CD40-ligand. Preferred vaccine adjuvants that can be administered with IL-15 and the vaccine are CD40-ligand and GM-CSF. Most preferred is GM-CSF. The additional adjuvant also can be administered in sequential or concurrent combination with IL-15 or the vaccine.

The IL-15 adjuvant compositions can be administered topically, orally, parenterally, rectally, by inhalation or by direct gene transfer. The term "parenteral" includes subcutaneous injections, intravenous, intramuscular, intracisternal injection, or infusion techniques. Administration of IL-15 can be done prior to, concurrent with or subsequent to the administration of the vaccine to the host. In any of the slow, controlled or sustained release formulations, IL-15 will normally be administered concurrently with the vaccine, although the release characteristics of IL-15 and the vaccine may differ in vivo. IL-15 can be administered from 5 days prior to vaccine administration to about 30 days post vaccine administration. Such compositions will typically contain an immunogenicity-augmenting amount of IL-15, alone or in combination with an effective amount of any other active material. The dosages and desired drug concentrations contained in the compositions may vary depending upon many factors, including the intended use, patient's body weight and age, and route of administration. Preliminary doses can be determined according to animal tests, and the scaling of dosages for human administration can be performed according to art-accepted practices without undue experimentation.

What is claimed is:

1. A method of enhancing a mammal's immune response to a vaccine antigen, comprising the steps of administering to such mammal an immunogenic amount of the vaccine antigen and an immunogenicity-augmenting amount of Interleukin-15 ("IL-15") in concurrent or sequential combination with such vaccine antigen.

2. A method according to claim 1, further comprising administering an immunogenicity-augmenting amount of an additional vaccine adjuvant in concurrent or sequential combination with the vaccine antigen and IL-15.

3. A method according to claim 2, wherein the additional vaccine adjuvant is a cytokine.

4. A method according to claim 3, wherein the additional vaccine adjuvant is selected from the group consisting of CD40-ligand, GM-CSF, G-CSF, IL-2, IL-4 and IL-10.

5. A method according to claim 4, wherein the additional vaccine adjuvant is GM-CSF.

6. A composition comprising an immunogenic amount of a vaccine antigen and an immunogenicity-augmenting amount of IL-15.

7. A composition according to claim 6 further comprising at least one additional vaccine adjuvant.

8. A composition according to claim 7, wherein the additional vaccine adjuvant is a cytokine.

9. A composition according to claim 8, wherein the additional vaccine adjuvant is selected from the group consisting of CD40-ligand, GM-CSF, G-CSF, IL-2 and IL-10.

10. A composition according to claim 9, wherein the additional vaccine adjuvant is GM-CSF.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
      ( A ) LENGTH: 489 base pairs
      ( B ) TYPE: nucleic acid
      ( C ) STRANDEDNESS: single
      ( D ) TOPOLOGY: linear ( i i ) MOLECULE TYPE: cDNA ( i x ) FEATURE:
    ( A ) NAME/KEY: CDS
    ( B ) LOCATION: 1..489

( x i ) SEQUENCE DESCRIPTION: SEQ ID NO:1:

```
ATG AGA ATT TCG AAA CCA CAT TTG AGA AGT ATT TCC ATC CAG TGC TAC        48
Met Arg Ile Ser Lys Pro His Leu Arg Ser Ile Ser Ile Gln Cys Tyr
 1               5                  10                  15

TTG TGT TTA CTT CTA AAC AGT CAT TTT CTA ACT GAA GCT GGC ATT CAT        96
Leu Cys Leu Leu Leu Asn Ser His Phe Leu Thr Glu Ala Gly Ile His
                20                  25                  30

GTC TTC ATT TTG GGC TGT TTC AGT GCA GGG CTT CCT AAA ACA GAA GCC       144
Val Phe Ile Leu Gly Cys Phe Ser Ala Gly Leu Pro Lys Thr Glu Ala
        35                  40                  45

AAC TGG GTG AAT GTA ATA AGT GAT TTG AAA AAA ATT GAA GAT CTT ATT       192
Asn Trp Val Asn Val Ile Ser Asp Leu Lys Lys Ile Glu Asp Leu Ile
    50                  55                  60

CAA TCT ATG CAT ATT GAT GCT ACT TTA TAT ACG GAA AGT GAT GTT CAC       240
Gln Ser Met His Ile Asp Ala Thr Leu Tyr Thr Glu Ser Asp Val His
 65                 70                  75                  80

CCC AGT TGC AAA GTA ACA GCA ATG AAG TGC TTT CTC TTG GAG TTA CAA       288
Pro Ser Cys Lys Val Thr Ala Met Lys Cys Phe Leu Leu Glu Leu Gln
                85                  90                  95

GTT ATT TCA CTT GAG TCC GGA GAT GCA AGT ATT CAT GAT ACA GTA GAA       336
Val Ile Ser Leu Glu Ser Gly Asp Ala Ser Ile His Asp Thr Val Glu
           100                 105                 110

AAT CTG ATC ATC CTA GCA AAC AAC AGT TTG TCT TCT AAT GGG AAT GTA       384
Asn Leu Ile Ile Leu Ala Asn Asn Ser Leu Ser Ser Asn Gly Asn Val
       115                 120                 125

ACA GAA TCT GGA TGC AAA GAA TGT GAG GAA CTG GAG GAA AAA AAT ATT       432
Thr Glu Ser Gly Cys Lys Glu Cys Glu Glu Leu Glu Glu Lys Asn Ile
   130                 135                 140

AAA GAA TTT TTG CAG AGT TTT GTA CAT ATT GTC CAA ATG TTC ATC AAC       480
Lys Glu Phe Leu Gln Ser Phe Val His Ile Val Gln Met Phe Ile Asn
145                 150                 155                 160

ACT TCT TGA                                                           489
Thr Ser
```

( 2 ) INFORMATION FOR SEQ ID NO:2:

( i ) SEQUENCE CHARACTERISTICS:
        ( A ) LENGTH: 162 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Arg Ile Ser Lys Pro His Leu Arg Ser Ile Ser Ile Gln Cys Tyr
 1               5                  10                  15

Leu Cys Leu Leu Leu Asn Ser His Phe Leu Thr Glu Ala Gly Ile His
                20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
 65                 70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
```

-continued-

|     |     |     | 100 |     |     |     |     | 105 |     |     |     | 110 |     |     |
|-----|-----|-----|-----|-----|-----|-----|-----|-----|-----|-----|-----|-----|-----|-----|
| Asn | Leu | Ile | Ile | Leu | Ala | Asn | Asn | Ser | Leu | Ser | Ser | Asn | Gly | Asn | Val |
|     |     | 115 |     |     |     |     | 120 |     |     |     | 125 |     |     |     |
| Thr | Glu | Ser | Gly | Cys | Lys | Glu | Cys | Glu | Glu | Leu | Glu | Glu | Lys | Asn | Ile |
|     | 130 |     |     |     |     | 135 |     |     |     |     | 140 |     |     |     |
| Lys | Glu | Phe | Leu | Gln | Ser | Phe | Val | His | Ile | Val | Gln | Met | Phe | Ile | Asn |
| 145 |     |     |     |     | 150 |     |     |     |     | 155 |     |     |     |     | 160 |
| Thr | Ser |     |     |     |     |     |     |     |     |     |     |     |     |     |     |